United States Patent [19]

List

[11] Patent Number: 5,221,265
[45] Date of Patent: Jun. 22, 1993

[54] ATTACHMENT PATCH

[75] Inventor: Harald List, Neuwied, Fed. Rep. of Germany

[73] Assignee: Lohmann GmbH & Co. KG, Neuwied, Fed. Rep. of Germany

[21] Appl. No.: 857,340

[22] Filed: Mar. 25, 1992

[30] Foreign Application Priority Data

Mar. 27, 1991 [DE] Fed. Rep. of Germany ... 9103742[U]

[51] Int. Cl.⁵ .............................................. A61M 25/02
[52] U.S. Cl. .................... 604/180; 128/DIG. 26
[58] Field of Search ................ 604/174, 180, 177; 128/640, DIG. 26

[56] References Cited

U.S. PATENT DOCUMENTS

| | | | |
|---|---|---|---|
| 2,159,947 | 5/1939 | Gansel | 128/DIG. 26 |
| 3,422,817 | 1/1969 | Mishkin et al. | 128/DIG. 26 |
| 3,683,911 | 8/1972 | McCormick | 604/180 |
| 3,918,446 | 11/1975 | Buttaravoli | 604/180 |
| 3,927,676 | 12/1955 | Schultz . | |
| 4,074,397 | 2/1978 | Rosin | 128/DIG. 26 |
| 4,275,721 | 6/1981 | Olson | 604/180 |
| 4,392,857 | 7/1983 | Beran | 128/DIG. 26 |
| 4,460,356 | 7/1984 | Moseley | 128/DIG. 26 |
| 4,534,762 | 8/1985 | Heyer . | |
| 4,915,694 | 4/1990 | Yamamoto et al. | 604/180 |
| 5,135,506 | 8/1992 | Gentelia et al. | 128/DIG. 26 |

FOREIGN PATENT DOCUMENTS 830113 7/1938 France .

*Primary Examiner*—Paul J. Hirsch
*Attorney, Agent, or Firm*—Collard & Roe

[57] ABSTRACT

An attachment patch for fastening medical accessories, such as cannulae, to the human skin, includes a carrier material provided with a pressure-sensitive adhesive layer, and a protective layer covering the pressure-sensitive adhesive layer and being provided with a lift-up type flap for fastening this cannula. The flap is divided into two fastening strips by a center cut, which preferably extends beyond the length of the flap.

11 Claims, 1 Drawing Sheet

ATTACHMENT PATCH

BACKGROUND OF THE INVENTION

1. Field of the Invention

The present invention relates to an attachment patch for fastening medical accessories such as catheters, cannulae, probes, drainages and the like to the human skin, comprising a carrier material provided with a pressure-sensitive adhesive layer and a protective layer covering the pressure-sensitive adhesive layer and being provided with an upward folding flap to keep the cannula in place.

2. The Prior Art

The typical accessories mentioned above, such as "cannulae" used in medical therapy, need to be reliably fixed. Very rarely, attachment is effected by sewing. In most cases, self-adhesive, partially pre-fabricated, and sometimes individually prepared, fastening strips are used. These known prior art solutions do not offer satisfactory results.

German Patent No. 31 05 187 (A1) describes a fastening means of this type, in which a patch is provided with an attachment strip in the form of a flap. This flap is formed by two parallel cuts starting from the edge of the patch toward the middle portion thereof and can be spirally wound around the cannula to be fixed after having been lifted up. Attachment of the cannula is thus achieved; however, stability and security of the resulting attachment are not satisfactory.

SUMMARY OF THE INVENTION

It is accordingly an object of the present invention to provide an attachment patch for fastening medical accessories which ensures simple, safe and stable attachment of the cannula.

This object is achieved according to the present invention by an attachment patch which includes a carrier material provided with a pressure-sensitive adhesive layer and a protective layer covering s id adhesive layer and which is provided with a lift-up flap to fasten the cannula.

This attachment patch is characterized by the following features: the flap is divided into two strips by a center cut, preferably extending beyond the length of the flap; the two strips can be pulled up and wound in opposite helical directions like a spiral around the cannula. The central cut preferably extends beyond the length of the flap, e.g., by one width of one of the resulting fastening strips, that the folding edges running diagonally to the direction of the flap and in opposite direction to each other assume the form of an arrowhead directed toward the end of the flap. Thus, the two strips formed by the central cut and provided with a lateral component, can be folded up mirror-invertedly about the diagonally extending folding lines.

Since the flap is partitioned by three unidirectional cuts starting from one narrow side of the attachment patch or, if the embodiment is a round patch, from any point along the patch edge, two fastening strips, as compared to the known attachment patch, can be wound like a spiral in opposite helical directions around the cannula to be held. Due to the folding edges running diagonally to the outside edges or boundary lines of the fastening strips, there are practically no creases formed when the strips are applied to the cannula.

In a preferred embodiment, the width of the flap consisting of the two fastening strips is determined in such a manner that, in the region of the folding edges, it at least corresponds to the diameter of the cannula to be attached. If the inner edges of the patch in the region of the folding edges are allowed to protrude slightly, even larger cannulae can be fastened.

In a further embodiment of the present invention, the protective layer is divided in such a manner that the protective strips covering the fastening strips may be separated from the rest of the protective layer and, preferably, pulled off individually. By means of this, the adhesive side of the fastening strips is protected from getting uncovered on pulling off the removable protective layer, which is made of suitable known materials, since this could make it more difficult to use and to apply the strips. In addition, the protective layer may optionally protect the actual patch in all directions to facilitate the handling thereof.

The shape and dimensions of the attachment patch according to the present invention are determined from the intended purpose of the application. The carrier material may be a textile fabric or a suitable film material. The known pressure-sensitive adhesives compatible with the skin are used as adhesives.

BRIEF DESCRIPTION OF THE DRAWINGS

Other objects and features of the present invention will become apparent from the following detailed description considered in connection with the accompanying drawing which discloses two embodiments of the present invention. It should be understood, however, that the drawing is designed for the purpose of illustration only and not as a definition of the limits of the invention.

In the drawing, wherein similar reference characters denote similar elements throughout the several views.

DETAILED DESCRIPTION OF PREFERRED EMBODIMENTS

Figure 1:
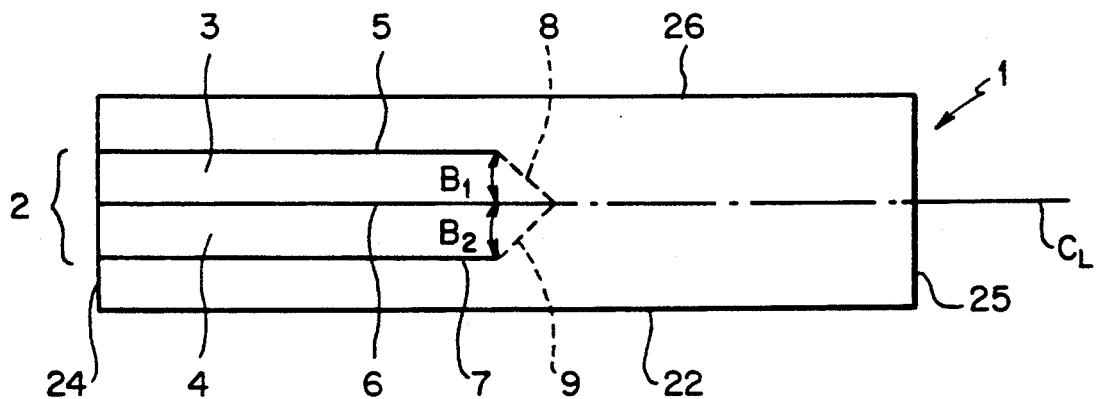
FIG. 1 is a top view of the attachment patch according to the present invention prior to application thereof to the skin.

Turning now in detail to the drawing, FIG. 1 shows a rectangular attachment patch 1 of FIG. 1 being provided with a flap 2 having the fastening strips 3 and 4. The flap 2 is formed by three unidirectional cuts 5, 6 and 7 running substantially parallel to the longitudinal sides 22 and 26 of the patch from one narrow side 24 of the patch 1 toward the other narrow side 25. Cut 6 is preferably along center line $C_L$ thereof. The central cut 6 extends beyond the lateral cuts 5, 7 by a length which approximately corresponds to the width of a fastening strip 3, 4 in the region of the folding edges 8, 9. When the fastening strips 3, 4 are pulled up, a folding edge 8 and 9, respectively, is created, each forming an angle A of approximately 45° to the direction of the cut. The folding edge lines 8, 9 together with the central cut 6 form a kind of arrow. Thus, substantially wrinkle-free application of the fastening strips 3, 4 to the cannula 11 shown in FIG. 2 is possible.

Furthermore, the cuts 5 and 7 forming the flap 2 generally run parallel to the longitudinal sides 22 and 26 of the attachment patch. They may also form a symmetric acute angle $B_1$ or $B_2$ thereto, preferably to the central cut 6. The acute angles $B_1$ or $B_2$ which are formed between the two outer cuts 5, 7 and the central cut 6 may run in such a way that the width of the fastening strips at the beginning of the cuts 5-7 is larger than that in the region of the folding edges 8 or 9, or vice-versa. In any case, the selection of the length, the width and the direction of width of the fastening strips depends on the actual intended purpose of the attachment patch 1 according to the present invention.

Figure 2:
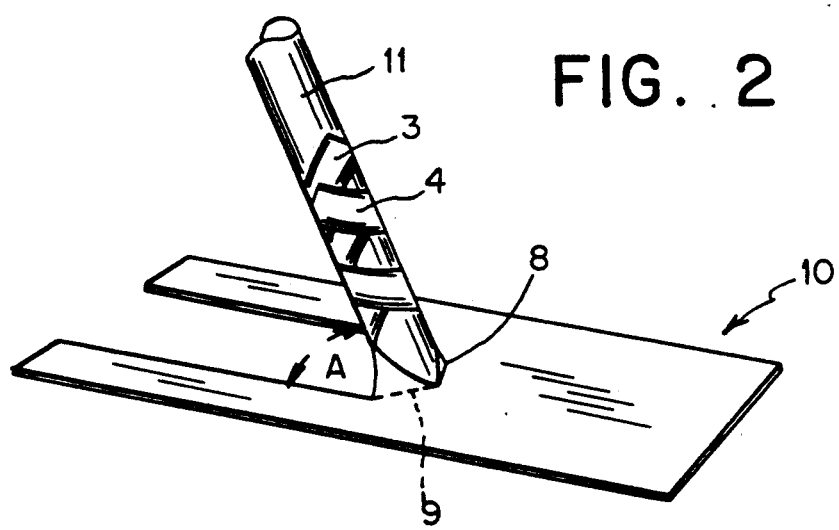
FIG. 2 is a perspective view of an applied patch according to FIG. 1.

FIG. 2 shows in perspective view a applied attachment patch 10 and a cannula 11 held by the fastening strips 3 and 4. These strips 3 and 4 are wound around the cannula 11 in a spiral helical direction in which each strip is wound oppositely to the other strip. The folding edges 8, 9 of patch 10 are moved near to the cannula 11 so that the cannula lies in the angle A formed by the folding edges 8, 9 of the lifted up fastening strips 3 and 4. Thus, it is possible to apply the fastening strips 3 and 4, which may be folded diagonally aside, to the cannula 11 without forming wrinkles. In particular, the cannula also forms the same angle A, preferably in the range of approximately 45°, to the adhesive area of the patch 10. The cannula 11 is thus safely and stably held by strips 3 and 4 and fixed into position.

Figure 3:
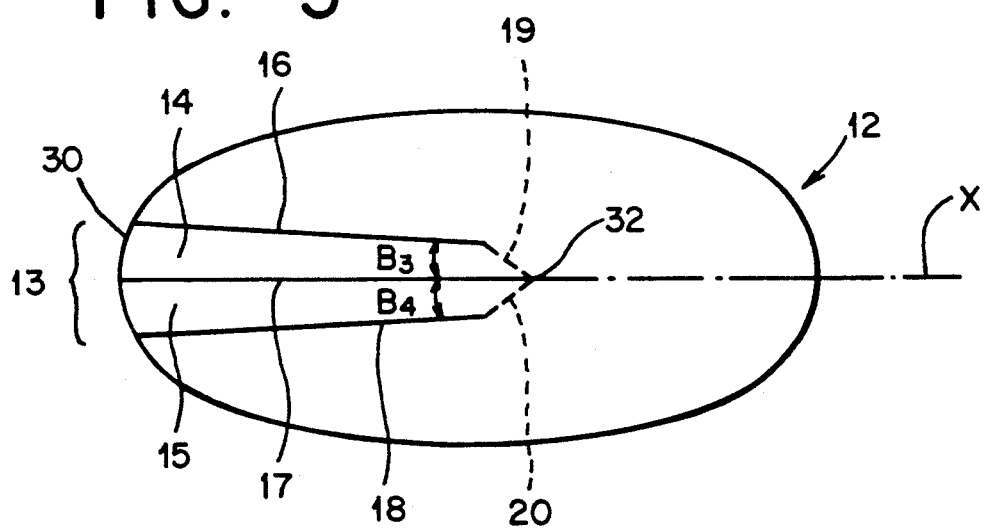
FIG. 3 is a top view of another embodiment of the attachment patch according to the present invention prior to application to the skin.

FIG. 3 shows, in another embodiment, an oval attachment patch 12 prior to application to the skin of the person. The cuts 16, 17 and 18 forming the fastening strips 14, 15 extend substantially in the direction of the major axis or the longitudinal axis X of the oval. They do not run parallel to each other, but are directed in such a way that the distance between the outer cuts 16 and 18 forming the flap 13 gradually decreases from the beginning 30 to the end 32 thereof. The outer cuts 16 and 18 may also run parallel to each other or to the central cut 17, or they may run in opposite directions. It is also preferred, however, that the central cut 17 lies on the major axis X and extends beyond the outer cuts 16 and 18 so that folding edges 19 and 20 of cuts 16 and 18, respectively, are formed which run diagonally to the central cut. This is preferably effected in the manner described above. Angles $B_3$ and $B_4$ in FIG. 3 correspond, respectively, to angles $B_1$ and $B_2$ of FIG. 1.

It should be noted that the shape and dimension of the attachment patch 1 or 12 according to the present invention as well as the shape and dimension of the flap 2 or 13, respectively, may be adapted to the individual requirements in any desired manner. This assumes that the flaps 2 or 13, respectively, is divided by the two independent fastening strips 3 or 4 and 14 or 15, respectively, and that this relationship is maintained.

The present invention has the advantages that the handling of the attachment patch according to the present invention is particularly simple and safe and that it can be produced simply and at a reasonable price. The attachment patch according to the present invention provides a safe and stable fastening means for medical accessories of the kind mentioned hereinbefore.

While only two embodiments of the present invention have been shown and described, it is to be understood that many changes and modifications may be made thereunto without departing from the spirit and scope of the invention as defined in the appended claims.

What is claimed is:

1. An attachment patch for fastening a medical accessory such as a cannula and the like to human skin, comprising
   a carrier material having a pressure-sensitive adhesive layer;
   a protective layer covering the pressure-sensitive adhesive layer, and
   said carrier material provided with a lift-up flap for holding said accessory in place; said flap being divided into two fastening strips by a central cut, and said flap having a length, with the central cut extending beyond the length of the flap.

2. The attachment patch according to claim 1, further comprising two lateral cuts with one on each side of the center cut;
   said central cut extending beyond the lateral cuts of equal length by such a distance, which is approximately the width of a fastening strip in the end portion of the cuts;
   said fastening strips foldable along a lateral component and having folding edges running diagonally to the direction of said fastening strips and in opposite direction to each other.

3. The attachment patch according to claim 1, wherein the patch has a narrow side with an edge;
   wherein the fastening strips are formed by three unidirectional cuts starting from the edge of a narrow side of the patch.

4. The attachment patch according to claim 3, wherein said patch is a round patch, said cuts are from any point of the patch edge and running substantially up to the center of the patch.

5. The attachment patch according to claim 2, wherein the width of the flap which is formed by the two fastening strips in the region of the folding edges at least corresponds to the diameter of the medical accessory to be held.

6. The attachment patch according to claim 5, further comprising longitudinal edges for the patch; wherein the cuts forming the flap run substantially parallel to the longitudinal edges of the patch.

7. The attachment patch according to claim 5, wherein the cuts forming the flap form an acute angle to the central cut which, with respect to said central cut, is a symmetric acute angle.

8. The attachment patch according to claim 7, wherein the acute angles which are formed by the two outer cuts with the central cut are placed such that the width of the fastening strips at the beginning of the cuts is larger than in the region of the folding edges, or vice versa.

9. The attachment patch according to claim 8, wherein the carrier material of the patch is a textile fabric.

10. The attachment patch according to claim 8 wherein the carrier material of the patch is a plastic film material.

11. The attachment patch according to claim 8 or 10 wherein said patch includes a fixing portion, said fixing portion and said fastening strips including said protective layer,
    wherein the protective layers of the fixing portion of the patch and of the fastening strips are removable independently of each other.

* * * * *